United States Patent
Jung et al.

(10) Patent No.: US 10,537,663 B2
(45) Date of Patent: Jan. 21, 2020

(54) PREPARATION METHOD OF HYDROGEL BASED ON DECELLULARIZED TISSUE USING SUPERCRITICAL FLUID-ORGANIC SOLVENT SYSTEM

(71) Applicant: KOREA INSTITUTE OF SCIENCE AND TECHNOLOGY, Seoul (KR)

(72) Inventors: Young Mee Jung, Seoul (KR); Soo Hyun Kim, Seoul (KR); Yoo Jin Seo, Seoul (KR)

(73) Assignee: Korea Institute of Science and Technology, Seoul (KR)

( * ) Notice: Subject to any disclaimer, the term of this patent is extended or adjusted under 35 U.S.C. 154(b) by 0 days.

(21) Appl. No.: 15/800,436

(22) Filed: Nov. 1, 2017

(65) Prior Publication Data

US 2018/0353648 A1 Dec. 13, 2018

(30) Foreign Application Priority Data

Jun. 13, 2017 (KR) .......................... 10-2017-0073815

(51) Int. Cl.
*A61L 27/00* (2006.01)
*A61L 27/36* (2006.01)
(Continued)

(52) U.S. Cl.
CPC ........... *A61L 27/3687* (2013.01); *A61L 27/24* (2013.01); *A61L 27/26* (2013.01); *A61L 27/3625* (2013.01);
(Continued)

(58) Field of Classification Search
CPC .................................................. A61L 27/3687
See application file for complete search history.

(56) References Cited

U.S. PATENT DOCUMENTS

| 2014/0004549 A1* | 1/2014 | Chen .................... | C12N 5/0068 435/23 |
| 2015/0315540 A1* | 11/2015 | Matthews ............ | C12N 5/0081 435/378 |

FOREIGN PATENT DOCUMENTS

| JP | 2007-105081 A | 4/2007 |
| KR | 10-2017-0003916 A | 1/2017 |

(Continued)

OTHER PUBLICATIONS

Crapo et al (Biomaterials 32 (2011) 3233-3243). (Year: 2011).*
(Continued)

*Primary Examiner* — Benjamin J Packard
(74) *Attorney, Agent, or Firm* — Rabin & Berdo, P.C.

(57) ABSTRACT

A method for preparing a decellularized tissue-based hydrogel with maximized ability of preserving various tissue-derived proteins, growth factors and cytokines by using a supercritical fluid-organic solvent system through (a) a step of decellularizing a biological tissue by bringing the same to contact with a supercritical fluid and an organic solvent at the same time; (b) a step of washing the decellularized tissue; (c) a step of preparing a decellularized tissue solution by mixing the washed decellularized tissue with one selected from an enzyme solution, an acidic solution and a mixture thereof; (d) a step of titrating the decellularized tissue solution to pH 5.5-7.8 by treating with a basic solution; and (e) a step of allowing the titrated decellularized tissue solution to stand at 30-40° C. and utilizing the same as a tissue engineering material with improved angiogenesis and tissue regeneration abilities.

9 Claims, 7 Drawing Sheets

(51) Int. Cl.
*A61L 27/52* (2006.01)
*A61L 27/24* (2006.01)
*A61L 27/26* (2006.01)

(52) U.S. Cl.
CPC .......... *A61L 27/3691* (2013.01); *A61L 27/52* (2013.01); *C12Y 301/00* (2013.01); *C12Y 304/23001* (2013.01); *C12Y 304/23002* (2013.01)

(56) References Cited

FOREIGN PATENT DOCUMENTS

KR           10-172514 B1    3/2017
WO      WO-2016024025 A1 *  2/2016    ......... A61L 27/3612

OTHER PUBLICATIONS

Harald C Ott et al., "Perfusion-decellularized matrix: using nature's platform to engineer a bioartificial heart", Nature Medicine, Feb. 2008, pp. 213-221, vol. 14, No. 2.

Yoshihide Hashimoto et al., "Preparation and characterization of decellularized cornea using high-hydrostatic pressurization for corneal tissue engineering", Biomaterials, 2010, pp. 3941-3948, vol. 31.

* cited by examiner

Collagen : dECM

PREPARATION METHOD OF HYDROGEL BASED ON DECELLULARIZED TISSUE USING SUPERCRITICAL FLUID-ORGANIC SOLVENT SYSTEM

CROSS-REFERENCE TO RELATED APPLICATIONS

This application claims priority under 35 U.S.C. § 119 to Korean Patent Application No. 10-2017-0073815 filed on Jun. 13, 2017 in the Korean Intellectual Property Office, the disclosure of which is incorporated herein by reference in its entirety.

TECHNICAL FIELD

The present disclosure relates to a method for preparing a decellularized tissue-based hydrogel using a supercritical fluid-organic solvent system, more particularly to a technology of preparing a decellularized hydrogel with maximized ability of preserving various tissue-derived proteins, growth factors and cytokines by using a supercritical fluid-organic solvent system and utilizing the same as a tissue engineering material with improved angiogenesis and tissue regeneration abilities.

BACKGROUND

Tissue engineering is an academic field for restoring, regenerating or substituting damaged or failed tissues and organs by using the basic concept and technology of the existing science fields, such as life science, medical science and engineering science, so that they may conduct normal functions. Recently, in the field of tissue engineering, the tissue-derived decellularized extracellular matrix (dECM) based on the decellularization technology is used for various applications, including not only ECM-based scaffolds of 2D or 3D structures but also bioink materials for 3D printing, etc.

In general, when decellularizing tissues or organs, they are treated with a surfactant or an enzyme, which is simple but has a strong effect, to remove the nuclei of cells. However, for SDS (sodium dodecyl sulfate), which is one of the surfactants, there are problems in that it denatures proteins that constitute the ECM, destroys the microstructure of the tissues and also removes various tissue-derived cytokines and growth factors, in addition to removing cell debris [non-patent document 1].

In order to overcome this limitation, a high pressure technology such as a hydrostatic pressure system or a supercritical fluid system is emerging as an alternative decellularization method. This decellularization method disrupts cells by applying high pressure. Therefore, the cell membrane can be disrupted without using a surfactant and no cytotoxic material remains in the decellularized extracellular matrix because no chemical substance is used.

The hydrostatic pressure system, which is one of the high pressure systems, decellularizes blood vessels and cornea. But, it requires application of high pressure up to 980 MPa and ice crystals formed in tissues after the decellularization process due to the use of water often lead to structural deformation of the extracellular matrix [non-patent document 2].

Accordingly, in order to improve the disadvantages of the easing method for preparing a tissue-derived decellularized extracellular matrix using a surfactant, the present disclosure is directed to preparing a decellularized hydrogel with maximized ability of preserving various tissue-derived proteins, growth factors and cytokines by using a supercritical fluid-organic solvent system and utilizing the same as a tissue engineering material with improved angiogenesis and tissue regeneration abilities.

REFERENCES

Non-Patent Documents

Non-patent document 1. Harald C. Ott et al., *Nature Medicine* 14, 213-221 (2008).
Non-patent document 2. Yoshihide Hashimoto et al., *Biomaterials* 31, 3941-3948 (2010).

SUMMARY

The present disclosure is designed to solve the problems described above and is directed to preparing a decellularized hydrogel with maximized ability of preserving various tissue-derived proteins, growth factors and cytokines by using a supercritical fluid-organic solvent system and utilizing the same as a tissue engineering material with improved angiogenesis and tissue regeneration abilities.

In an aspect, the present disclosure provides a method for preparing a decellularized tissue-based hydrogel, including: (a) a step of decellularizing a biological tissue by bringing the same to contact with a supercritical fluid and an organic solvent at the same time; (b) a step of washing the decellularized tissue; (c) a step of preparing a decellularized tissue solution by mixing the washed decellularized tissue with one selected from an enzyme solution, an acidic solution and a mixture thereof; (d) a step of titrating the decellularized tissue solution to pH 5.5-7.8 by treating with a basic solution; and (e) a step of allowing the titrated decellularized tissue solution to stand at 30-40° C.

In an exemplary embodiment of the present disclosure, the biological tissue may be selected from the heart, spleen, liver, lung, stomach, brain, fat, bone, pancreas, ovary, small intestine, large intestine, colon, blood vessel and esophagus of a mammal.

In another exemplary embodiment of the present disclosure, the method may further include, before the step (a), a step of freeze-drying the biological tissue and immersing the same in an organic solvent for 5-20 hours.

In another exemplary embodiment of the present disclosure, the supercritical fluid may be carbon dioxide and the organic solvent may be ethanol.

In another exemplary embodiment of the present disclosure, the decellularization may be performed by adding the biological tissue into a reactor containing the organic solvent, injecting the supercritical fluid such that the pressure in the reactor is 300-400 bar and then bringing the same to contact at 23-42° C. for 2-24 hours.

In another exemplary embodiment of the present disclosure, in the step (b), the decellularized tissue may be washed with a PBS buffer containing a DNase.

In another exemplary embodiment of the present disclosure, the enzyme may be pepsin and the acidic solution may be acetic acid.

In another exemplary embodiment of the present disclosure, the acidic solution may be 0.1-1 M acetic acid and the basic solution may be sodium hydroxide.

In another exemplary embodiment of the present disclosure, in the step (c), the decellularized tissue solution may be prepared by mixing the washed decellularized tissue and the acidic solution at a weight ratio of 10-50:1.

In another exemplary embodiment of the present disclosure, in the step (c), the decellularized tissue solution may be prepared by further mixing with one or more gel selected from collagen, fibrin, Matrigel, alginate, PuraMatrix, polyethylene glycol gel, poly(NIPAM), poloxamer, chitosan, agarose, gelatin and hyaluronic acid.

In another exemplary embodiment of the present disclosure, the gel may be collagen and the collagen may be prepared into a collagen solution by mixing the collagen and deionized water at a weight ratio of 1-5:1.

In another exemplary embodiment of the present disclosure, a volume ratio of the collagen solution and the decellularized tissue solution may be 1-9:9-1.

In another exemplary embodiment of the present disclosure, in the step (e), the titrated decellularized tissue solution may be allowed to stand for 20-60 minutes.

In another exemplary embodiment of the present disclosure, the tissue may be a heart tissue; the method may further include, before the step (a), a step of freeze-drying the biological tissue and immersing the same in an organic solvent for 10-16 hours; the supercritical fluid may be carbon dioxide and the organic solvent may be ethanol; the decellularization may be performed by adding the biological tissue into a reactor containing the organic solvent, injecting the supercritical fluid such that the pressure in the reactor is 300-400 bar and then bringing the same to contact at 35-40° C. for 3-9 hours; in the step (b), the decellularized tissue may be washed with phosphate-buffered saline (PBS) containing a DNase; the acidic solution may be 0.3-0.7 M acetic acid and the basic solution may be sodium hydroxide; in the step (c), the decellularized tissue solution may be prepared by mixing the washed decellularized tissue and the acidic solution at a weight ratio of 20-40:1; in the step (c), the decellularized tissue solution may be prepared by mixing the washed decellularized tissue with a collagen solution containing collagen and deionized water at a weight ratio of 2-4:1; a volume ratio of the collagen solution and the decellularized tissue solution may be 3-5:5-7; and, in the step (e), the titrated decellularized tissue solution may be allowed to stand for 30-50 minutes.

According to the present disclosure, a decellularized hydrogel with maximized ability of preserving various tissue-derived proteins, growth factors and cytokines may be prepared by using a supercritical fluid-organic solvent system and it may be utilized as a tissue engineering material with improved angiogenesis and tissue regeneration abilities.

DETAILED DESCRIPTION OF EMBODIMENTS

Figure 1:
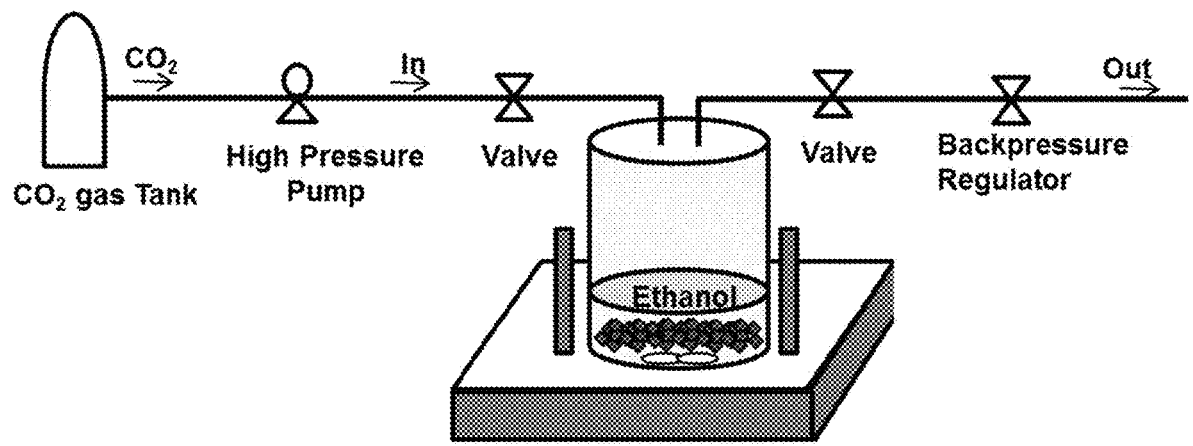
FIG. 1 schematically shows a supercritical fluid-organic solvent reaction system of the present disclosure used in Example 1.

Hereinafter, various aspects and exemplary embodiments of the present disclosure are described in more detail.

An aspect of the present disclosure relates to a method for preparing a decellularized tissue-based hydrogel, including: (a) a step of decellularizing a biological tissue by bringing the same to contact with a supercritical fluid and an organic solvent at the same time; (b) a step of washing the decellularized tissue; (c) a step of preparing a decellularized tissue solution by mixing the washed decellularized tissue with one selected from an enzyme solution, an acidic solution and a mixture thereof; (d) a step of titrating the decellularized tissue solution to pH 5.5-7.8 by treating with a basic solution; and (e) a step of allowing the titrated decellularized tissue solution to stand at 30-40° C.

The method for preparing a decellularized tissue-based hydrogel using a supercritical fluid-organic solvent system according to the present disclosure is advantageous in that a decellularized tissue-based hydrogel containing tissue-derived factors in large quantities can be prepared because the degree of denaturation of proteins is low, the ability of preserving growth factor, cytokines and tissue-derived proteins is superior and the supercritical fluid and the organic solvent do not remain after the decellularization.

In an exemplary embodiment of the present disclosure, the biological tissue may be selected from the heart, spleen, liver, lung, stomach, brain, fat, bone, pancreas, ovary, small intestine, large intestine, colon, blood vessel and esophagus of a mammal, although not being limited thereto.

In another exemplary embodiment of the present disclosure, the method may further include, before the step (a), a step of freeze-drying the biological tissue and immersing the same in an organic solvent for 5-20 hours, specifically for 10-16 hours.

Through this step, the solubility of the tissue in the supercritical fluid or the organic solvent may be increased.

In another exemplary embodiment of the present disclosure, the supercritical fluid may be carbon dioxide and the organic solvent may be ethanol.

Carbon dioxide is an inexpensive reagent which is non-toxic and nonflammable and can be used with high purity. It acts as a supercritical fluid exhibiting the properties of a gas and a liquid at the same time at temperatures and pressures above the critical point ($T_c$=31.1° C., $P_c$=73.8 bar).

Because the liquid-like density of carbon dioxide increases solubility whereas its gas-like viscosity allows fast diffusion, a supercritical carbon dioxide-organic solvent system dissolves the phospholipid constituting the cell membrane and the nuclear membrane in a tissue, thereby disrupting a cell.

As the organic solvent, one or more alcohol-based solvent selected from ethanol, methanol and propanol may be used, although not being limited thereto. Specifically, ethanol may be used.

In another exemplary embodiment of the present disclosure, the decellularization may be performed by adding the biological tissue into a reactor containing the organic solvent, injecting the supercritical fluid such that the pressure in the reactor is 300-400 bar, specifically 330-370 bar, and then bringing the same to contact at 23-42° C., specifically 35-40° C., for 2-24 hours, specifically 3-9 hours.

After the contacting is completed, the supercritical fluid-organic solvent system may be removed from the tissue by discharging the supercritical fluid-organic solvent system out of the reactor.

Because the above-described temperature range is the biological temperature range, the ability of preserving proteins, cytokines and growth factors in the biological tissue may be improved.

In another exemplary embodiment of the present disclosure, in the step (b), the decellularized tissue may be washed with a PBS buffer containing a DNase.

The DNase (deoxyribonuclease) is an enzyme which specifically acts on DNA and degrades DNA through hydrolytic cleavage of phosphodiester linkages. By washing the decellularized tissue with a PBS buffer containing the DNase, the DNA released out of the cell membrane disrupted by the high pressure can be degraded and the tissue can be washed.

The washing may be performed for 1-10 days, specifically 3-8 days, more specifically 4-6 days.

In another exemplary embodiment of the present disclosure, the enzyme may be pepsin and the acidic solution may be acetic acid.

In another exemplary embodiment of the present disclosure, the acidic solution may be 0.1-1 M acetic acid and the basic solution may be sodium hydroxide.

The acidic solution may be one or more selected from acetic acid, hydrochloric acid, p-toluenesulfonic acid and maleic acid. But, any solution may be used as long as pH can be adjusted to 2.5-4.5 without being limited thereto. Specifically, acetic acid or hydrochloric acid may be used. Most specifically, acetic acid may be used.

And, specifically, an aqueous solution containing one or more acid selected from those described above at a concentration of 0.1-1 M may be used. More specifically, 0.3-0.7 M acetic acid may be used.

The basic solution may be one or more selected from sodium hydroxide, sodium carbonate, sodium bicarbonate, disodium hydrogen phosphate, calcium bicarbonate, calcium hydroxide, calcium hydroxide nitrate, calcium hydroxide chloride, calcium hydroxide cyanide, potassium hydroxide, ammonium hydroxide and sodium acetate. But, any solution may be used as long as pH can be adjusted to 5.5-7.8 without being limited thereto. Specifically, sodium hydroxide may be used.

The basic solution serves to titrate acidity and adjust pH to 5.5-7.8, specifically 6.5-7.5, similarly to the biological pH in order to reduce inflammatory responses of nearby cells when the hydrogel is used for subcutaneous injection or as a scaffold for tissue engineering.

In another exemplary embodiment of the present disclosure, in the step (c), the decellularized tissue solution may be prepared by mixing the washed decellularized tissue and the acidic solution at a weight ratio of 10-50:1.

As a specific example, the decellularized tissue solution may be prepared by mixing the washed decellularized tissue with liquid nitrogen, pulverizing the mixture into a fine powder and then mixing the same with the acidic solution for 30-60 hours, specifically 40-55 hours, to a concentration of 1-50 mg/mL, specifically 5-40 mg/mL.

In another exemplary embodiment of the present disclosure, in the step (c), the decellularized tissue solution may be prepared by further mixing with one or more gel selected from collagen, fibrin, Matrigel, alginate, PuraMatrix, polyethylene glycol gel, poly(NIPAM), poloxamer, chitosan, agarose, gelatin and hyaluronic acid, although not being limited thereto. Specifically, collagen may be used.

In another exemplary embodiment of the present disclosure, the gel may be collagen and the collagen may be prepared into a collagen solution by mixing the collagen and deionized water at a weight ratio of 1-5:1.

The decellularized tissue prepared using the supercritical fluid-organic solvent system exhibits better preservation of tissue-derived proteins and growth factors as well as less weight reduction before and after the decellularization as compared to the existing decellularization using a surfactant because the tissue components are not dissolved by the surfactant. Accordingly, the decellularized tissue prepared using the supercritical fluid-organic solvent system has a smaller content of collagen per unit tissue weight. Collagen is the protein which plays a critical role in gelation during the preparation of a tissue-based hydrogel. Due to the small collagen content per unit tissue weight, gelation is difficult for the decellularized tissue prepared using the supercritical fluid-organic solvent system. In order to overcome this problem, the decellularized tissue may be mixed with the gel described above in order to further improve the physical properties of the prepared decellularized tissue-based hydrogel.

In another exemplary embodiment of the present disclosure, the gel may be collagen and the collagen may be prepared into a collagen solution by mixing the collagen and one selected from deionized water, a sodium hydroxide solution and phosphate-buffered saline (PBS) at a weight ratio of 1-10:1.

In another exemplary embodiment of the present disclosure, a volume ratio of the collagen solution and the decellularized tissue solution may be 1-9:9-1.

In particular, when the decellularized tissue solution and the collagen solution are mixed with the above-described weight ratio and, at the same time, when the volume ratio of the collagen solution and the decellularized tissue solution is the above range, it exhibits superior angiogenesis ability. In contrast, when the weight ratio of any of the decellularized tissue solution and the collagen solution is outside the above range or when the volume ratio of the collagen solution and the decellularized tissue solution is outside the above range, angiogenesis ability is decreased significantly.

In another exemplary embodiment of the present disclosure, in the step (e), the titrated decellularized tissue solution may be allowed to stand for 20-60 minutes, specifically 30 minutes or longer.

Although not clearly specified in Examples or Comparative Examples, decellularized tissue-based hydrogels were prepared from various types of biological tissues using the supercritical fluid-organic solvent system while varying conditions such as the freeze-drying before the decellularization, the immersion time in the organic solvent, the supercritical fluid and the organic solvent, the pressure, temperature and contact time in the reactor during the decellularization, the solution for washing the decellularized tissue, the acidic solution and the basic solution, the mixing ratio of the decellularized tissue and the acidic solution in the decellularized tissue solution, the mixing of the decellularized tissue solution with the collagen solution, the mixing ratio of the collagen and the deionized water, the volume ratio of the collagen solution and the decellularized tissue solution and the time during which the decellularized tissue solution was allowed to stand. The prepared decellularized tissue-based hydrogels were subcutaneously injected into rats and the degree of degradation by body fluid was monitored.

As a result, degradation by body fluid did not occur in vivo and the hydrogels remained intact even after 90 days when the following conditions were satisfied: (i) the biological tissue is a heart tissue, (ii) before the step (a), the biological tissue is freeze-dried and then immersed in the organic solvent for 10-16 hours, (iii) the supercritical fluid is carbon dioxide, (iv) the organic solvent is ethanol, (v) the decellularization is performed by adding the biological tissue into a reactor containing the organic solvent, injecting the supercritical fluid such that the pressure in the reactor is 300-400 bar and then bringing the same to contact at 35-40° C. for 3-9 hours, (vi) in the step (b), the decellularized tissue is washed with phosphate-buffered saline (PBS) containing a DNase, (vii) the acidic solution is 0.3-0.7 M acetic acid, (viii) the basic solution is sodium hydroxide, (ix) in the step (c), the decellularized tissue solution is prepared by mixing the washed decellularized tissue and the acidic solution at a weight ratio of 20-40:1, (x) in the step (c), the decellularized tissue solution is prepared by mixing the decellularized tissue solution with a collagen solution containing collagen and deionized water at a weight ratio of 2-4:1, (xi) the volume ratio of the collagen solution and the decellularized tissue solution is 3-5:5-7 and (xii), in the step (e), the titrated decellularized tissue solution is allowed to stand for 30-50 minutes.

When any of the above conditions was not satisfied, the hydrogels were degraded by body fluid within 7 days.

Hereinafter, the present disclosure is described in detail referring to preparation examples, examples and attached drawings.

Example 1: Preparation of Decellularized Heart Tissue

First, 100 mg of freeze-dried rat heart tissue was immersed in ethanol for at least 12 hours in order to increase the reactivity of the tissue with supercritical carbon dioxide and ethanol.

Then, the heart tissue was put in a high pressure reactor for a supercritical fluid-organic solvent process and then reacted with supercritical carbon dioxide by adding ethanol. After increasing the reactor temperature to 35° C., carbon dioxide was injected using a high pressure pump until the pressure inside the reactor reached 350 bar. Then, the reactor temperature was set to 37° C. The pressure was maintained for 6 hours so that the carbon dioxide and the ethanol infiltrated into the heart tissue.

After the reaction was completed, the carbon dioxide and the ethanol were removed from the tissue by opening the valve. The decellularized heart tissue taken out of the reactor was washed with a PBS buffer containing a DNase for 5 days.

Examples 2-1 and 2-2: Preparation of Decellularized Heart Tissue-Based Hydrogel

A hydrogel was prepared by mixing with collagen to improve the physical properties of the decellularized heart tissue-based hydrogel. The decellularized heart tissue prepared in Example 1 was added to liquid nitrogen, pulverized into a fine powder and then dissolved in 0.5 M acetic acid to a concentration of 30 mg/mL, thereby preparing a decellularized tissue solution. As a collagen, a collagen solution prepared by diluting in deionized water to a concentration of 3 mg/mL was used.

Because the two gels are sensitive to temperature, the collagen solution and the decellularized tissue solution were mixed in an icebox. After neutralizing with sodium hydroxide, the mixture was allowed to stand at 37° C. for at least 30 minutes to prepare a hydrogel.

The mixing ratio of the collagen solution and the decellularized tissue solution was 7:3 and 5:5 for Examples 2-1 and 2-2, respectively.

Comparative Example 1: Preparation of Decellularized Heart Tissue Using Surfactant A decellularized heart tissue was prepared using a surfactant according to the method described in the literature (*Nature Medicine* 14, 213-221 (2008)).

Comparative Example 2: Collagen Solution

A collagen solution was prepared by diluting a collagen gel in deionized water to a concentration of 3 mg/mL.

Figure 2A:
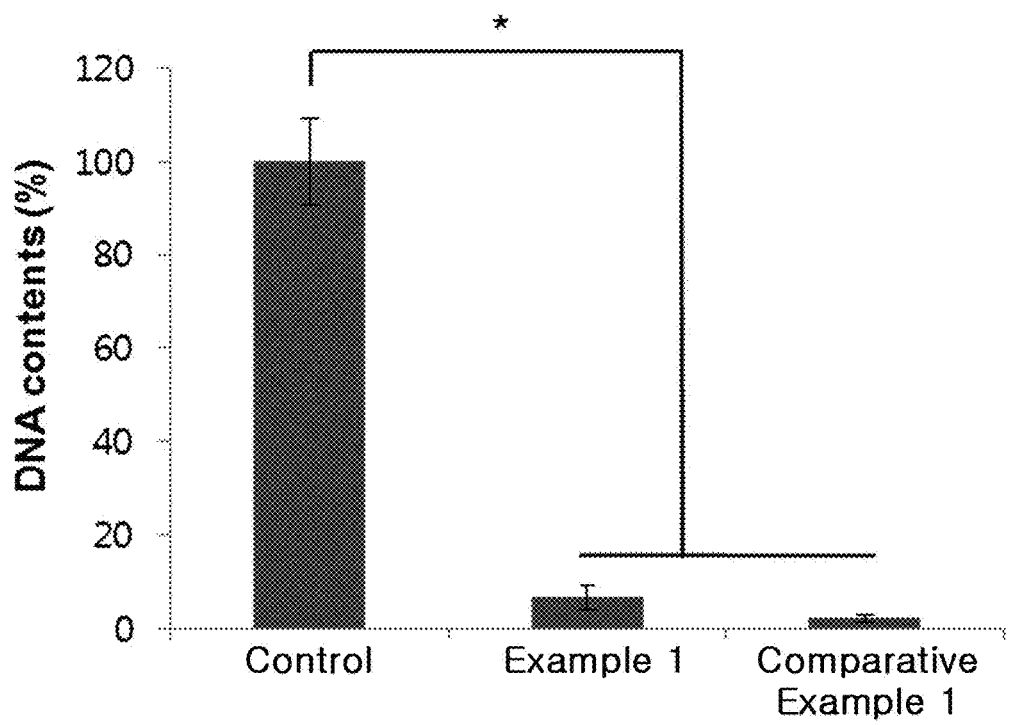
FIGS. 2A and 2B show results of quantifying DNA and staining cell nuclei of a decellularized heart tissue of the present disclosure prepared in Example 1, a decellularized heart tissue prepared in Comparative Example 1 and a control group.
Figure 2B:
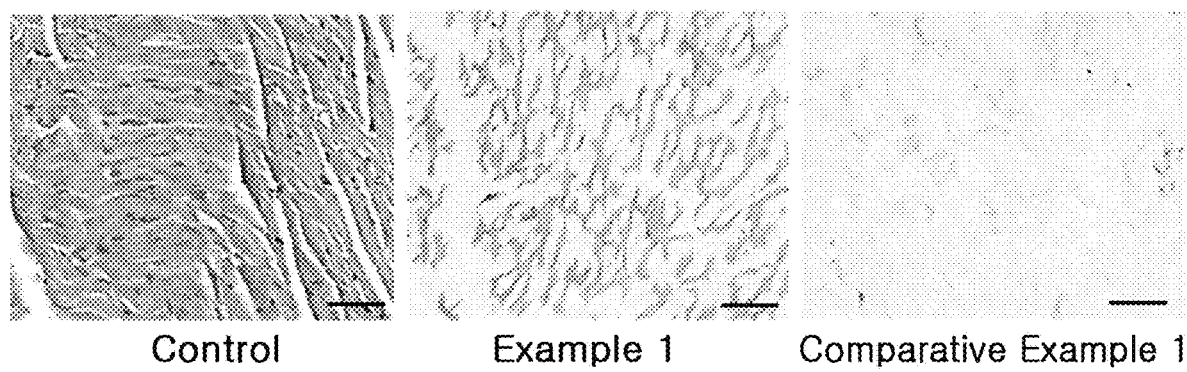

FIGS. 2A and 2B show results of quantifying DNA and staining cell nuclei of the decellularized heart tissue of the present disclosure prepared in Example 1, the decellularized heart tissue prepared in Comparative Example 1 and a control group.

Referring to FIGS. 2A and 2B, it can be seen that the DNA and cell nuclei hardly remain in the decellularized heart tissues of Example 1 and Comparative Example 1 as compared to the control group.

Figure 3A:
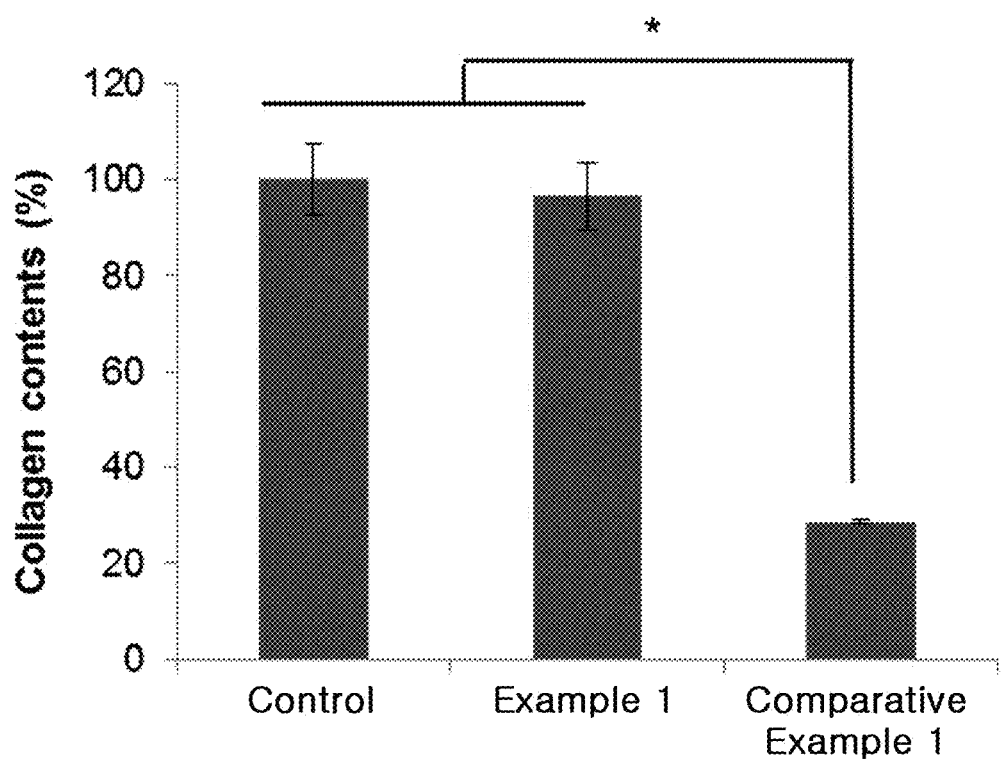
FIGS. 3A and 3B show results of quantifying collagen and glycosaminoglycan (GAG) of a decellularized heart tissue of the present disclosure prepared in Example 1, a decellularized heart tissue prepared in Comparative Example 1 and a control group.
Figure 3B:
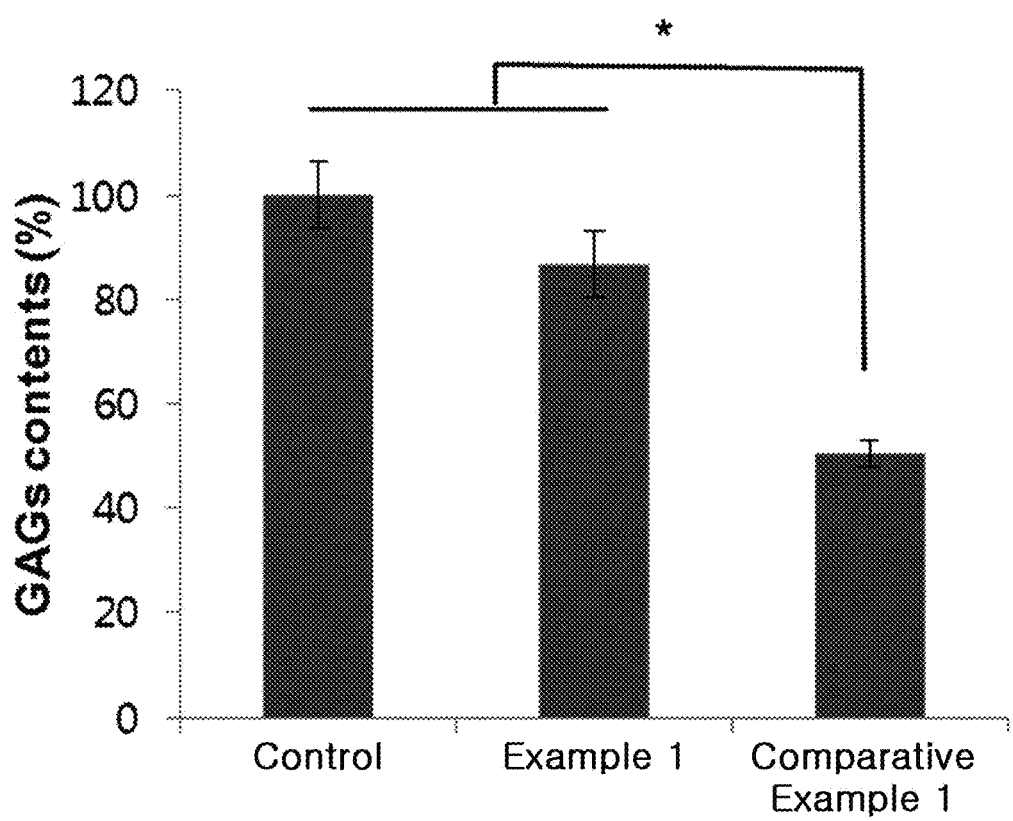

FIGS. 3A and 3B show results of quantifying collagen and glycosaminoglycan (GAG) of the decellularized heart tissue of the present disclosure prepared in Example 1, the decellularized heart tissue prepared in Comparative Example 1 and a control group.

Referring to FIGS. 3A and 3B, it can be seen that the decellularized heart tissue of Example 1 exhibits significantly better ability of preserving collagen and glycosaminoglycan as compared to Comparative Example 1.

Figure 4A:
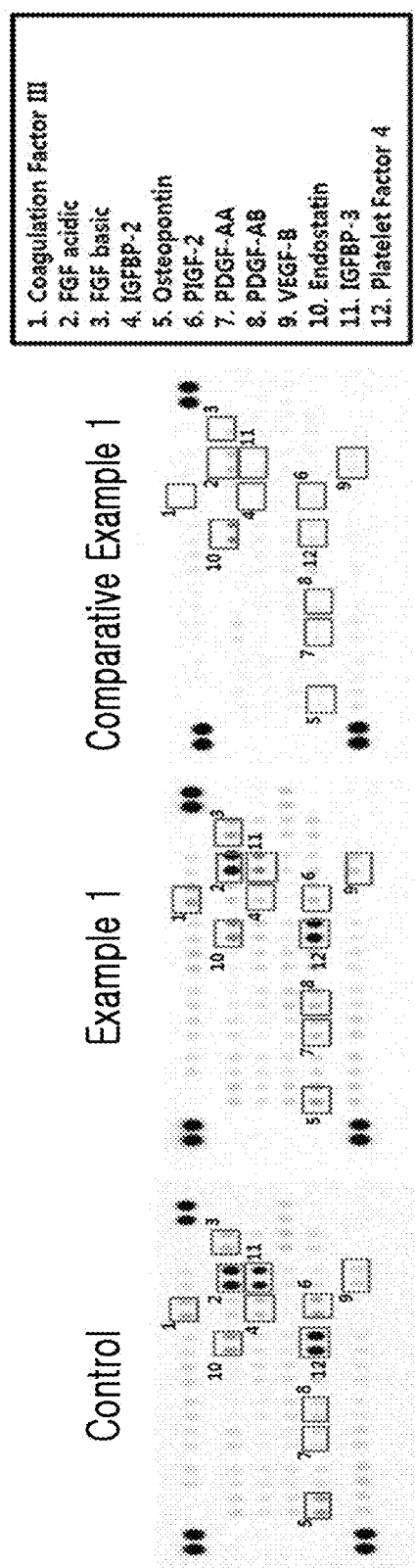
FIGS. 4A and 4B show angiogenic factors of a decellularized heart tissue of the present disclosure prepared in Example 1, a decellularized heart tissue prepared in Comparative Example 1 and a control group.
Figure 4B:
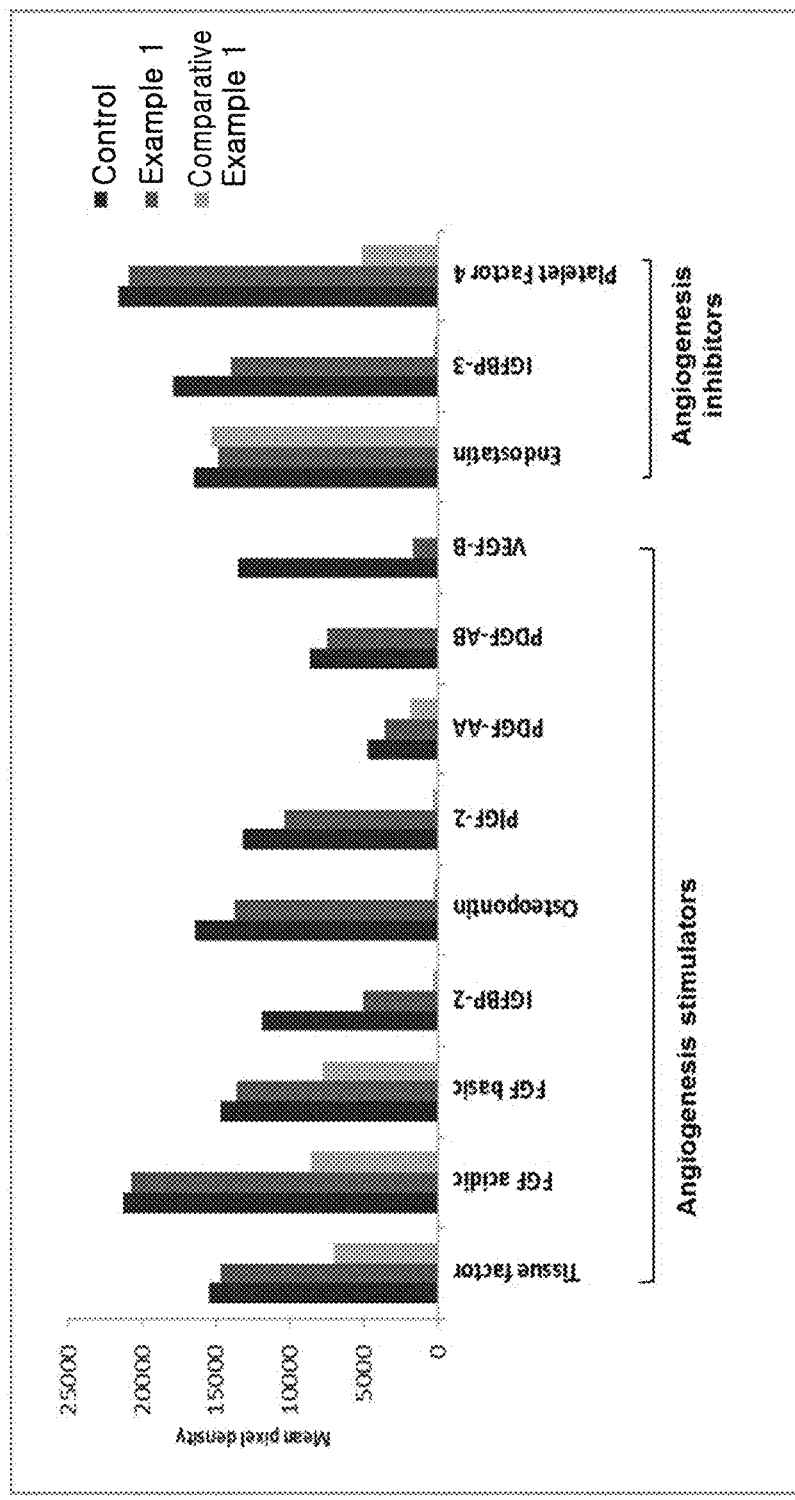

FIGS. 4A and 4B shows angiogenic factors of the decellularized heart tissue of the present disclosure prepared in Example 1, the decellularized heart tissue prepared in Comparative Example 1 and a control group.

Referring to FIGS. 4A and 4B, it can be seen that the decellularized heart tissue of Example 1 exhibits significantly better ability of preserving various angiogenic factors as compared to Comparative Example 1.

Figure 5:
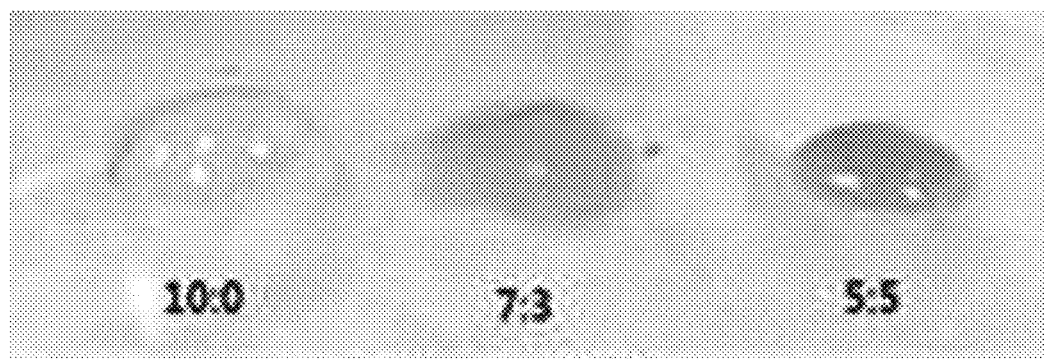
FIG. 5 shows images of decellularized heart tissue-based hydrogels of the present disclosure prepared in Examples 2-1 and 2-2, with different mixing ratios of a collagen solution and a decellularized tissue solution, and a collagen solution of Comparative Example 2.

FIG. 5 shows images of the decellularized heart tissue-based hydrogels of the present disclosure prepared in Examples 2-1 and 2-2, with different mixing ratios of the collagen solution and the decellularized tissue solution, and the collagen solution of Comparative Example 2.

Referring to FIG. 5, it can be seen that a hydrogel was not formed when the volume ratio of the collagen solution and the decellularized tissue solution was 7:3, due to weak physical properties. It can be seen that, the hydrogel structure was formed well when the volume ratio was 5:5.

According to the present disclosure, a decellularized hydrogel with maximized ability of preserving various tissue-derived proteins, growth factors and cytokines may be prepared by using a supercritical fluid-organic solvent system and it may be utilized as a tissue engineering material with improved angiogenesis and tissue regeneration abilities.

What is claimed is:
1. A method for preparing a decellularized tissue-based hydrogel, comprising:
    (a-1) a step of freeze-drying a biological tissue and immersing the same in an organic solvent for 5-20 hours;

(a) a step of decellularizing a biological tissue by bringing the same to contact with a supercritical fluid and an organic solvent at the same time;
(b) a step of washing the decellularized tissue;
(c) a step of preparing a decellularized tissue solution by mixing the washed decellularized tissue with one selected from an enzyme solution, an acidic solution and a mixture thereof, wherein,
the decellularized tissue solution is prepared by mixing the washed decellularized tissue and the acidic solution at a weight ratio of 10-50:1, then, mixing with a collagen solution,
the collagen solution comprises collagen and deionized water at a weight ratio of 1-5:1, and
a volume ratio of the collagen solution and the decellularized tissue solution is 5:5;
(d) a step of titrating the decellularized tissue solution to pH 5.5-7.8 by treating with a basic solution; and
(e) a step of allowing the titrated decellularized tissue solution to stand at 30-40° C.

2. The method for preparing a decellularized tissue-based hydrogel according to claim 1, wherein the biological tissue is selected from the heart, spleen, liver, lung, stomach, brain, fat, bone, pancreas, ovary, small intestine, large intestine, colon, blood vessel and esophagus of a mammal.

3. The method for preparing a decellularized tissue-based hydrogel according to claim 1, wherein the supercritical fluid is carbon dioxide and the organic solvent is ethanol.

4. The method for preparing a decellularized tissue-based hydrogel according to claim 1, wherein the decellularization is performed by adding the biological tissue into a reactor comprising the organic solvent, injecting the supercritical fluid such that the pressure in the reactor is 300-400 bar and then bringing the same to contact at 23-42° C. for 2-24 hours.

5. The method for preparing a decellularized tissue-based hydrogel according to claim 1, wherein, in the step (b), the decellularized tissue is washed with a PBS buffer comprising a DNase.

6. The method for preparing a decellularized tissue-based hydrogel according to claim 1, wherein the enzyme is pepsin and the acidic solution is acetic acid.

7. The method for preparing a decellularized tissue-based hydrogel according to claim 1, wherein the acidic solution is 0.1-1 M acetic acid and the basic solution is sodium hydroxide.

8. The method for preparing a decellularized tissue-based hydrogel according to claim 1, wherein, in the step (e), the titrated decellularized tissue solution is allowed to stand for 20-60 minutes.

9. The method for preparing a decellularized tissue-based hydrogel according to claim 1,
wherein
the tissue is a heart tissue;
the method further comprises, before the step (a), a step of freeze-drying the biological tissue and immersing the same in an organic solvent for 10-16 hours;
the supercritical fluid is carbon dioxide and the organic solvent is ethanol;
the decellularization is performed by adding the biological tissue into a reactor comprising the organic solvent, injecting the supercritical fluid such that the pressure in the reactor is 300-400 bar and then bringing the same to contact at 35-40° C. for 3-9 hours;
in the step (b), the decellularized tissue is washed with phosphate-buffered saline (PBS) comprising a DNase;
the acidic solution is 0.3-0.7 M acetic acid and the basic solution is sodium hydroxide;
in the step (c), the decellularized tissue solution is prepared by mixing the washed decellularized tissue and the acidic solution at a weight ratio of 20-40:1;
in the step (c), the decellularized tissue solution is prepared by mixing the washed decellularized tissue with a collagen solution comprising collagen and deionized water at a weight ratio of 2-4:1; and
in the step (e), the titrated decellularized tissue solution is allowed to stand for 30-50 minutes.

\* \* \* \* \*